United States Patent [19]

Horn

[11] Patent Number: 5,061,059
[45] Date of Patent: Oct. 29, 1991

[54] SELF-DETECTION GLAUCOMA TEST METHOD

[76] Inventor: Gerald Horn, 74 Golf Rd., Golf, Ill. 60029

[21] Appl. No.: 616,770

[22] Filed: Nov. 15, 1990

Related U.S. Application Data

[63] Continuation of Ser. No. 315,401, Feb. 23, 1989, abandoned.

[51] Int. Cl.$^5$ .............................................. A61B 3/02
[52] U.S. Cl. ................................... 351/223; 351/224; 351/226
[58] Field of Search ............... 351/223, 224, 225, 226, 351/246

[56] References Cited

U.S. PATENT DOCUMENTS

| | | | |
|---|---|---|---|
| 1,903,502 | 4/1933 | Campbell | 351/226 |
| 3,827,789 | 8/1974 | Molner | 351/224 |
| 3,837,734 | 9/1974 | Regan | 351/225 |
| 4,737,024 | 4/1988 | Damato | 351/224 |
| 4,798,456 | 1/1989 | Enoch | 351/224 |

Primary Examiner—Rodney B. Bovernick
Attorney, Agent, or Firm—Jones, Day, Reavis & Pogue

[57] ABSTRACT

A method for the detection of glaucoma which permits the early detection of glaucoma without expensive equipment or a technician. The device for the method comprises a planar surface having a fixation target thereon for focusing a test eye during testing, a mark positioned in a blind spot area outside of the user's area of peripheral vision and at least one additional mark in the field of vision of the user. To perform the method for the determination of glaucoma, the user of the device focuses the test eye on the fixation target eliminating the mark in the blind spot area from the user's vision and ascertaining the visibility of each additional mark.

4 Claims, 3 Drawing Sheets

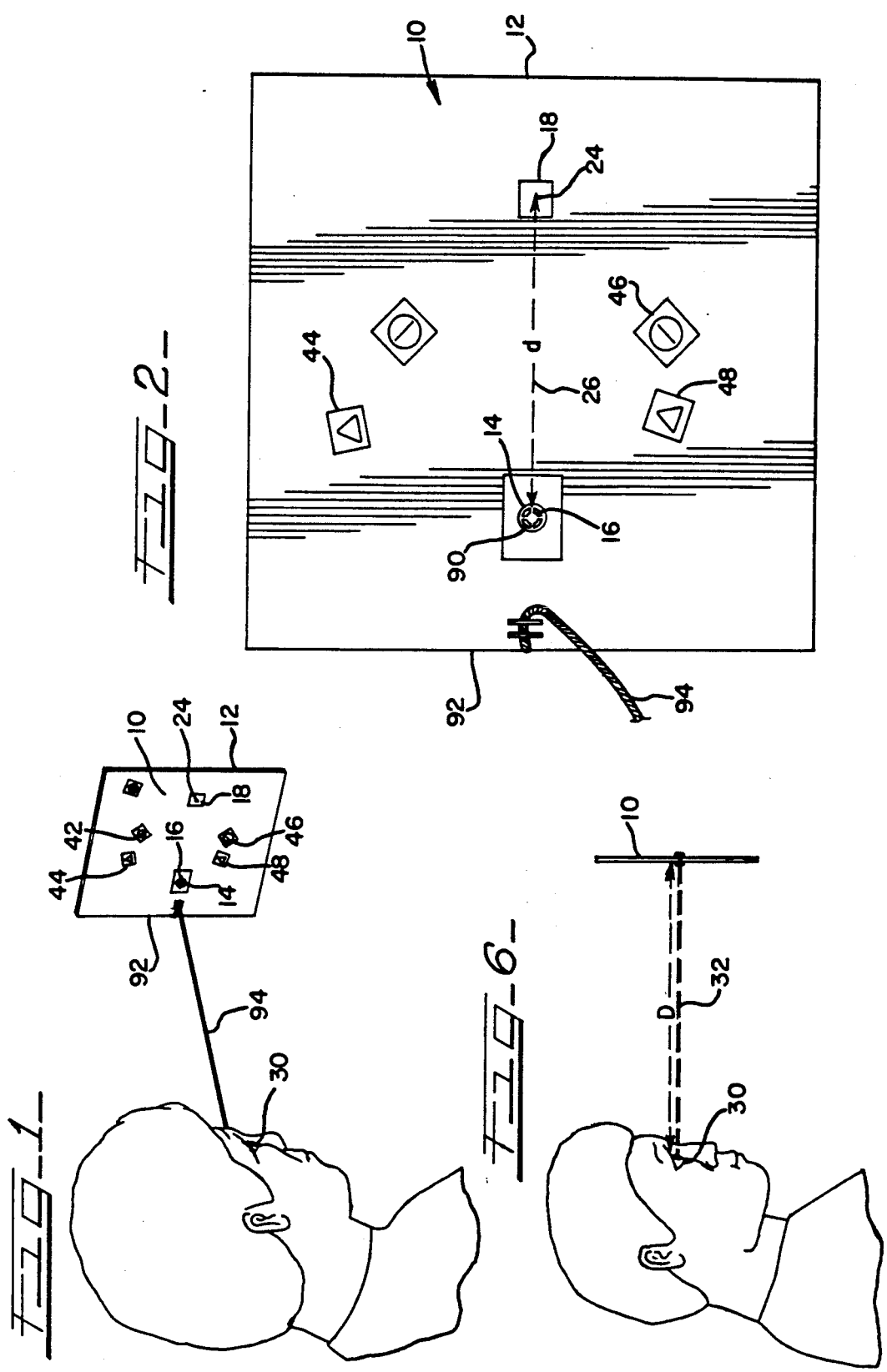

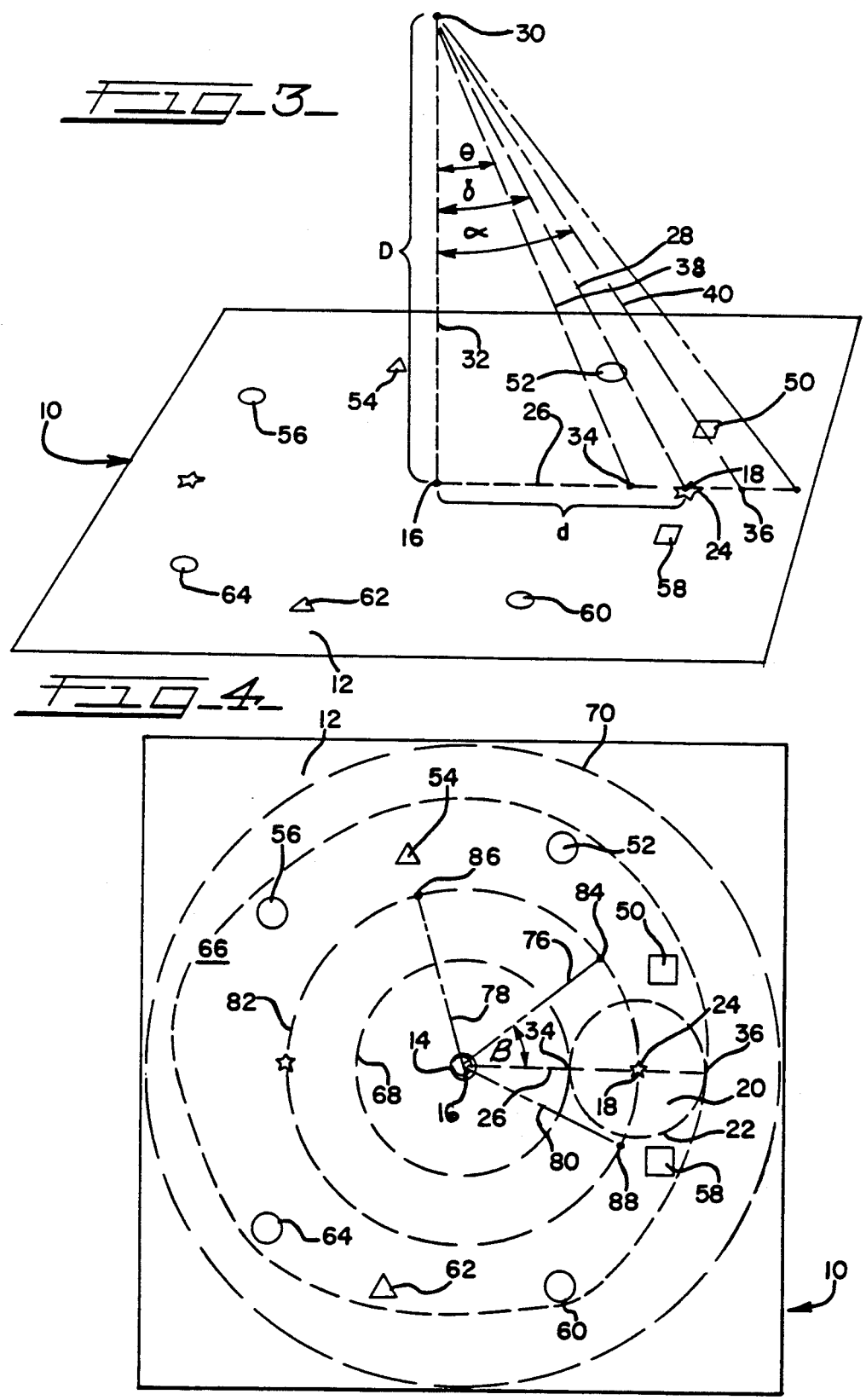

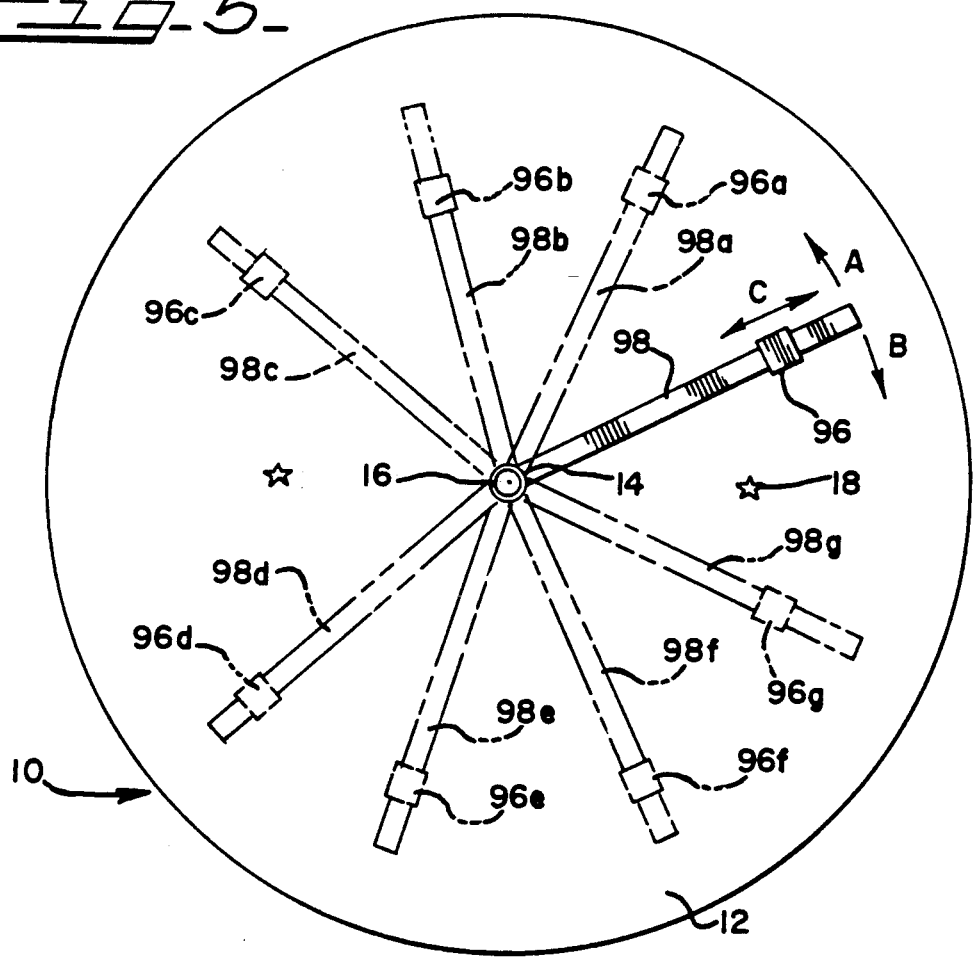

SELF-DETECTION GLAUCOMA TEST METHOD

This is a continuation of copending application Ser. No. 07/315,401 filed on Feb. 23, 1989, now abandoned.

BACKGROUND OF THE INVENTION

This invention relates to self-testing for the presence of glaucoma. In particular, it relates to a device and a method whereby one can detect the presence of glaucoma without the need of outside assistance.

Glaucoma is a prevalent affliction of the eye that can occur in anyone at any time and is a condition in which vision may become permanently lost. By far, the most common type of glaucoma is chronic simple glaucoma which is painless, slowly progressive and virtually undetectable by the individual particularly in its stages when it is most easily and sucessfully treated. Most individuals with glaucoma only become aware of it at a time when all that remains is tunnel vision due to its gradual, painless and progressive course when untreated.

With normal peripheral vision, at any given distance from the eye, a blind spot exists at a predetermined distance just temporal to a target point at which the eye is fixated. Most of the earliest scotomas in glaucoma (i.e., small circumscribed areas of dimness or actual loss of visual field) occur in a narrow region radiating generally arcuately from just outside this blind spot above and below the point of fixation. Advanced glaucoma changes are present when multiple scotomas in this region begin to coalesce after which they extend beyond the region itself and eventually encroach on or eliminate central vision.

Present visual testing for glaucoma requires sophisticated devices to accurately create a map, which is a graphic depiction of the extent of the field of vision, with any areas in which peripheral vision is diminished or absent well demarcated. These visual field tests require a technician to administer the test. The patient looks at a central fixation target and indicates when a light can be seen with side vision. These tests can be very accurate but they are often difficult to administer properly since they are tedious—often taking twenty minutes or more per eye—and it is difficult to completely prevent the patient from looking directly at the source of light which is the peripheral target rather than remaining fixed on a central target and using side vision to detect the light. One of these tests, the tangent screen, is a simple test, but it too has the same fixation problem and requires a technician.

It is therefore an object of the present invention to provide a procedure for detecting early glaucoma without the need of special equipment.

Still another object of the present invention is to develop a device for the self-determination of glaucoma which does not require a technician to perform the test.

Still another object of the present invention is to provide a simplified, low-cost, portable device for the determination of the presence of glaucoma.

Another object of the present invention is the development of a method and device for detecting glaucoma which can be used in the home, thus increasing the chances of early detection, long before one would normally become aware of and seek treatment for permanent glaucomatous vision loss.

Other objects and advantages of the present invention will become apparent from the ensuing description.

SUMMARY OF THE INVENTION

The present invention is directed to a device and method for the self-detection of the presence of glaucoma in the human eye. This device comprises a planar surface or viewing plane having a fixation target thereon with a first mark also positioned on the surface at a defined distance from the fixation target. The first mark is located in a small area which is undetectable within the normal field of vision of a test eye of a user of the device. This area is termed "the blind spot area" and is positioned just temporal to the test eye when the eye is focused on the fixation target from a predetermined distance along an imaginary, substantially vertical line of sight. As employed herein, the term "temporal" signifies an angular direction, relative to vertical, extending outwardly from a test eye of a user of the present devices toward the adjacent temple area on the side of the skull of the user. That is, the temporal direction is opposite to the "nasal" direction which extends at an angle from the test eye toward the nose of a user of the device.

More specifically, the blind spot area in which the first mark is situated is generally bounded by an imaginary circular section on the planar surface centered at a blind spot center point. This blind spot center point is defined for any given fixation point as the point of intersection of an imaginary horizontal line segment through the fixation point lying in the viewing plane with a first imaginary line of sight extending from the eye to be tested to the planar surface at an angle of about 12.5° temporal to the aforementioned imaginary, substantially vertical line of sight between the test eye and the fixation point.

The diameter of the imaginary circular section circumscribing the blind spot area is dependent on two other imaginary lines of sight radiating at specific angles temporal to the substantially vertical line of sight and the points of intersection of these two other imaginary lines with the above referenced horizontal line segment. That is, one end point of the diameter of the circular section is defined as the point of intersection of one of the other imaginary lines of sight extending at an angle of about 10° temporal to the vertical line of sight with the horizontal line segment while the other end point of the diameter of this circular section is defined as the point of intersection of the second of the other imaginary lines of sight extending at an angle of about 15° temporal to the vertical line of sight with the horizontal line segment.

The devices of this invention further include at least one additional mark on the planar surface. However, in a preferred embodiment of the invention, at least four additional marks are positioned on the planar surface and, most preferably, eight such marks are so positioned. It is further preferred to position an equal number of marks on the surface above and below the aforementioned imaginary horizontal line segment through the blind spot center point and the fixation point. In the event that a single additional mark is employed, it is preferred that such mark constitute a movable symbol or object which may be relocated from one position on the surface to a variety of other positions in order to enable testing of the ability of the test eye to detect visibility of marks at multiple locations about the surface of the device.

In this regard, it should be noted that whether a single mark or multiple marks is utilized, each of such additional marks is positioned within the normal field of peripheral vision of a test eye of a user of the device when that eye is focused on the fixation target. Thus, if the test eye is not afflicted with glaucoma, the additional mark or marks would be visible to the user of the device under normal circumstances. However, to the extent that any mark or marks is not visible, the user will be able to quickly determine any deficency in vision field within the area in which the earliest symptoms of glaucoma occur and to detect this indication of the onset of glaucoma.

More specifically, each of the additional marks is positioned on the planar surface along an imaginary path wherein early scotomas in glaucoma appear. In particular, these additional marks are placed within a region bounded by two concentric circular shapes each of which is defined as the intersection of an imaginary right circular cone with the planar surface. These two right circular cones are formed by rotating imaginary lines of sight radiating from the test eye about an axis essentially perpendicular to the planar surface. This axis comprises the imaginary, substantially vertical line of sight between the test eye and the fixation point and the line of rotation utilized to form the inner right circular cone essentially corresponds to the imaginary line of sight radiating from the test eye at an angle of about 10° relative to the substantially vertical axis which defines one end point of the diameter of the circular section. On the other hand, the line of rotation employed to form the outer right circular cone is an imaginary line of sight radiating from the test eye at an angle not greater than about 30° relative to the substantially vertical axis. However, in order to reduce the size of the sheet constituting the planar surface and to achieve a hand-held device (for example, having a square shaped surface of about 12"×12" or less), it has been found that the angle forming the outer cone should not exceed 25° relative to the vertical axis.

In a most preferred embodiment of this invention, the outer boundary for the additional marks comprises an imaginary arcuate shape defined by the intersection with the planar surface of a cone of revolution about the same substantially vertical axis as previously described. This cone of revolution is formed by rotating an imaginary line of sight radiating from the test eye about the substantially vertical axis at varying angles defined in accordance with the following equation:

$$\alpha \simeq 15° + \beta/18$$

wherein $\alpha$ is the angle between the axis and the line of sight radiating from the test eye and $\beta$ is an angle formed between radial lines on the planar surface extending from the fixation point as the central point of a circle to various points along the circumference of the circle with the radius of the circle corresponding to the distance between the fixation point and the blind spot center point and the angle $\beta$ is symmetrically measured in degrees from a horizontal base line extending between the fixation point and the blind spot center point in a clockwise or a counterclockwise direction whereby $\beta$ ranges from 0° at the blind spot center point to 180° maximum in either direction around the circumference of the circle.

In accordance with the foregoing equation, a line being rotated about the axis to define the cone of revolution resulting in the arcuate shape would extend from the vertical axis at an angle relative thereto of about 15° when the angle $\beta$ is 0°; at an angle of about 16° when $\beta$ is 18°; at an angle of 20° when $\beta$ is 90°; at an angle of 21° when $\beta$ is 108° and 25° when $\beta$ is 180° and these calculations apply whether the angle $\beta$ is measured in a clockwise or a counterclockwise direction from the base line.

Another requirement for the placement of the additional marks is that they all must be situated outside of the blind spot area (i.e., the entire shape of the mark must not overlap any point within the blind spot area). In this regard, it has been found that in a preferred embodiment of the present invention, the center of any of the additional marks should be positioned at a point wherein $\beta$ is at least 20° removed from the horizontal base line either clockwise or counterclockwise therefrom. Furthermore, it has been found that none of the additional marks should be positioned so that their centers are positioned at a point wherein $\beta$ would exceed 170° in either a clockwise or a counterclockwise direction from the base line. With these exceptions, the placement of the additional marks about the planar surface of the device of this invention within the area bounded by the inner circle and the outer arc for the testing of scotomas caused by glaucoma is considered to be essentially arbitrary and a matter of individual choice. However, a sufficient number of such marks is required within this area to enable detection of even relatively small scotomas.

Each of the marks included on the surface of the device has a distinct form surrounding a center point thereof and may consist of any geometric shape desired such as a square, a circle, a triangle, a rectangle or the like. However, symmetrical shapes surrounding the center points of the marks are preferred as opposed to asymmetrical shapes. The size of the marks is, likewise subject to choice; but, if a square is employed, a dimension of about ⅜" to about ¾" per side is preferred; if a circular shape is employed, the diameter of the circle preferrably should be about ⅜" to about ¾"; and if a triangular shape is employed, then the sides preferrably should range in size from about ⅜" to about ¾".

Additionally, it is known that contrast sensitivity is decreased in glaucoma. Thus, the marks on the surface of the device advantageously are depicted as contrast targets or objects in order to facilitate the sensitivity of the instant glaucoma test. The object contrast is related to the reflectivity difference between the object and an equal area object the color of the background. Thus, if the absolute reflectivity of the object is defined as $R_o$ and the absolute reflectivity of the same area object colored the same as the background is defined as $R_b$, then the percent contrast (% C) can be calculated according to the following equation:

$$\%C = \frac{(R_b - R_o)100}{R_b}$$

Any given object can be composed of different areas $(A_i)$, each with its own reflectivity per unit area $(S_i)$ controlled by the color or degree of gray. Thus, the absolute reflectivity of the object $(R_o)$ may be expressed as follows:

$$R_o = \Sigma A_i S_i$$

The marks may be solid single color objects of low contrast or line figures which have well defined shapes and low contrast or a combination of both. For example, the percent contrast (% C) of a non-solid colored object such as an annulus having a thin dark line or ring defining the annulus and a center the same color as the background can be calculated in accordance with the following equations when the annulus has an inner radius (R), a ring thickness (t) and the inner area is of a color (w) having reflectivity ($S_w$) with the ring of a different color (d) and reflectivity ($S_d$):

$$R_o = \pi R^2 S_w + (2\pi Rt + \pi t^2) S_d \text{ and } R_b = \pi (R + t)^2 S_w$$

$$\%C = \frac{S_w - S_d}{S_w} \frac{(2\pi Rt + \pi t^2)100}{[\pi (R + t)^2]}$$

Thus, in an exemplary preferred embodiment of the present invention, R=0.50" and t=0.02" with $S_w$=0.95 and $S_d$=0.05 which results in a % C=7.1.

Additionally, in early stages of glaucoma, there is often a decrease in sensitivity to particular colors, such as blue, so that such a colored object or mark can have a larger contrast than is needed for colors which are not decreased in their sensitivity to detection by a user of the device. Consequently, a device can be composed of objects or marks which are of either type. It has been found that low contrast marks composed of colors without decreased sensitivity (for example, black, gray or white) which have a contrast range of 5-20% are sensitive for detection of early glaucoma. In a preferred embodiment, line figures are employed having 6-9% contrast. For those marks which have colors having reduced detection sensitivity (such as blue), the contrast range could increase to 100%, and in a preferred embodiment such objects would range from 5-50%.

Larger degrees of contrast can be used for detecting the progressive field loss in a user of the device with pre-existing glaucoma who has failed a low contrast version of the devices of the present invention. In such case, the device can use higher contrast objects or marks designed to provide early detection of additional visual field loss in a user of the device with pre-existing glaucoma. A device of this nature can use higher contrast symbols with a range of 9-100%, whose contrast depends on the degree of visual loss which is being monitored by the early detection device.

If desired, the fixation target may be fabricated of reflective material in an attempt to assure that the user's eye will remain fixated as required for the proper use of the present device. The presence of a cross-hair on the fixation target has also been found to be useful in maintaining the focus of the eye on the fixation target although it too has been found not to be essential. Also, a string, tape or other material of a predetermined length can optionally be attached to the device so the user will know the exact distance that the present device should be held from his eye during the test.

In using the present devices, the individual need only close one eye and, with the other eye, look directly at the fixation target from a proper distance to eliminate the mark in the true blind spot from his peripheral vision. The disappearance of this mark within the user's field of vision assures the user that the test is being properly administered. Then, while the open eye remains focused on the fixation target and the mark within the blind spot area continues to be removed from the user's field of vision, the user determines the visibility of the additional marks which should be in his field of vision. However, if at any time during the test, the user should stop directing his focus on the fixation target then the blind spot mark would reappear within the user's visual field warning of an improper test condition.

In accordance with this invention, the distance between the test eye and the fixation target should be from about three to about four times the distance between the fixation target and the blind spot center point on the device.

BRIEF DESCRIPTION OF THE DRAWINGS

FIG. 1 is a perspective view of an individual using a device in accordance with the present invention to detect the presence of glaucoma, the device being equipped with an optional measuring element for positioning a test eye a predetermined distance from the surface of the device;

FIG. 2 is a top plan view of the device of FIG. 1;

FIG. 3 is a schematic view illustrating various imaginary lines of sight radiating from a test eye of a user of a device of the present invention and showing the intersection of these lines of sight with the planar surface of the device to define various points and boundary lines for placement of the marks and other indicia thereon;

FIG. 4 is a top plan view of an embodiment of a device of the present invention produced in accordance with the constructs of FIG. 3 which further illustrates the imaginary boundary lines on the planar surface of the device utilized for placement of the various targets, marks and other indicia on such surface;

FIG. 5 is a top plan view of another embodiment of a device in accordance with the present invention; and FIG. 6 is a side elevation showing the use of a hand-held embodiment of a device in accordance with the present invention.

DETAILED DESCRIPTION

Referring to the drawings, the present device 10 for the self-detection of glaucoma is illustrated. The device 10 is constructed from a planar sheet 12 constituting a viewing plane having a fixation target 14 thereon which surrounds a central target point 16. A first mark 18 spaced from the fixation target 14 is positioned on the sheet 12 in a blind spot area 20 of a user of the device 10.

The blind spot area 20 is bounded by an imaginary circular section 22 (as best illustrated in phantom in FIG. 4) on the planar surface 12. This circular section 22 is centered at a blind spot center point 24. As further illustrated in FIGS. 3 and 4, the blind spot center point 24 is positioned at the point of intersection of an imaginary horizontal line segment 26 which extends from the fixation target 14 and lies in the viewing plane 12 with a first imaginary line of sight 28 extending from an eye to be tested 30 to the blind spot center point 24 on the planar surface 12 at an angle γ of about 12.5° temporal to an imaginary substantially vertical line of sight 32 between the test eye 30 and the fixation target point 16.

The diameter of the circular section 22 which constitutes the boundary of the blind spot area 20 is defined by the points of intersection 34,36 of two other imaginary lines of sight 38 and 40 with the horizontal line segment 26. As illustrated in FIG. 3, these lines 38 and 40 radiate from test eye 30 at angles temporal to the substantially vertical line of sight 32 designated θ and α, respectively. In accordance with the present invention, the angle θ is about 10°. The angle α, as will be discussed hereinafter, will vary depending on the position of intersection of line 40 with the planar surface 12. However, when line 40 extends from eye 30 to the point of intersection constituting one end point of the diameter of circular section 22 along the horizontal line segment 26, the angle α will measure about 15°.

As illustrated, the mark 18 is spaced from the target 14 a distance d which is measured between the central target point 16 and the blind spot center point 24. This distance d is controlled by the distance D corresponding to the length of the line of sight 32 between the test eye 30 and the fixation target point 16 during the use of the present device 10 in testing the eye for glaucoma. In order to have sufficient spacing between the fixation target 14 and the mark 18, the fixation target 14 can be positioned anywhere on the sheet 12, either centrally or off-center, closer to the edge of the sheet 12. Preferably, however, the target 14 is positioned to permit the placement of the remaining indicia on the planar surface 12 and the construction of a portable device 10 that can be used at a reasonable distance from the eye being tested for glaucoma and, most preferably, within arms length of the user of the device 10.

The ratio of the distance D between the test eye 30 and the fixation target point 16 to the distance d between the fixation target point 16 and the blind spot center point 24 within mark 18 should be between about three and four. This means that the distance d is between about 0.25 and 0.33 of the distance D. However, in order to provide a portable device 10 which may conveniently be used to self-determine glaucoma, the distance d should not be too long, for otherwise the required distance D between the device 10 and the eye 30 will be considerably longer than the user's arm. For convenience, this distance d should be between about two inches and six inches, preferably between about three inches and five inches. It has been found that, if this distance d is about 4⅛ inches, then the test eye 30 during the test should be between about 15.5 and 16.25 inches from the target 14 for best test results.

As illustrated in FIGS. 1 and 2, the device 10 has four additional marks 42–48 positioned on the planar surface 12. Furthermore, in another embodiment of this invention, as illustrated in FIGS. 3 and 4, a total of eight such marks 50–64 of varying shapes and sizes are positioned on the surface 12 with an equal number of marks positioned above and below the horizontal line 26. Regardless of the number of such additional marks, it is to be noted that they will all be positioned, as best illustrated in FIG. 4, within a region 66 bounded by two concentric imaginary circular shapes 68,70 with circle 68 defining an inner boundary and circle 70 defining an outer boundary of region 66. This region 66 is wholly within the visual field of a user of the device 10 who is not afflicted with glaucoma and it corresponds generally to the path in which a high percentage of early scotomas in glaucoma can be expected to appear within the normal field of peripheral vision.

The circular shapes 68 and 70 defining the boundaries of region 66 are formed as previously detailed. Specifically, inner circular shape 68 and outer circular shape 70 are formed as the intersections of imaginary right circular cones (not shown) with the planar surface 12 where the circular cone for circle 68 is formed by rotating line of sight 38 which radiates from eye 30 at an angle of about 10° relative to the essentially vertical line of sight 32 about the axis provided by such line 32 and the circular cone for circle 70 is formed by similarly rotating a line of sight 72 which radiates from eye 30 at an angle of about 30° relative to line of sight 32 about the axis provided by such line 32.

However, in order to minimize the dimensions of the sheet 12 employed for the device 10, it has been found to be preferable to reduce the outer circular shape 70 to a smaller diameter. In this regard, it has been found that an outer circular shape formed by rotating the line 72 about the axis provided by line 32 at an angle less than 30° and, preferably, less than 25° relative to line 32 can be utilized without adversely impacting the efficacy of the glaucoma test procedures herein. Furthermore, in a most preferred embodiment of this invention wherein the practical consideration of sheet dimension is contemplated along with the necessity for providing accurate and useful diagnostic results with the devices 10, it has been found that the outer boundary for positioning the additional marks 42–48 or 50–64, for example, should be defined by an imaginary outer arcuate shape 74 as best illustrated in FIG. 4.

The outer arcuate shape 74 is formed as the intersection of an imaginary cone of revolution (not shown) with the planar surface 12 where the cone of revolution is formed by rotating imaginary line of sight 36 radiating from eye 30 about the axis provided by the imaginary line 32 at varying angles relative to such axis as defined in accordance with the equation:

$$\alpha \approx 15° + \beta/18$$

wherein, as illustrated in FIG. 3, α is the angle formed between line 32 and line 36 and β is an angle formed between radial lines such as lines 76,78 and 80 on the planar surface 12 extending from the fixation target point 16 as the central point of imaginary circle 82 to various points 84,86,88 along the circumference of the circle 82 with the radius of the circle corresponding to the distance d between the fixation point 16 and the blind spot center point 24 and the angle β is symmetrically measured in degrees from the horizontal line 26 in a clockwise or a counterclockwise direction whereby β ranges from 0° at the blind spot center point 24 to 180° maximum in either direction around the circumference.

As previously noted, in order to better evaluate the presence of glaucoma in the test eye, it is helpful that at least two of the marks 42,44 or 50,52,54,56, as illustrated, be above and at least two of the marks 46,48 or 58,60,62,64, as illustrated, be beneath the horizontal line 26. Furthermore, it is preferred that all of the marks 42–48 and 50–64 be smaller than the size of the blind spot area 20. In particular, mark 18 should be of a smaller size than the size of the blind spot area 20. For convenience, its size can be about ⅓ of the diameter of the circular section 22 of the blind spot area 20.

Thus, for example, with a spacing d of about 4⅛ inches between the fixation target point 16 and the blind spot center point 24 and the diameter of the circular section 22 of the blind spot area 20 being about 1½ inches, mark 18 should have a size of ½ inch by ½ inch or less in a preferred embodiment of this invention. In the example of the device 10 having a 4⅛ inch distance d and with the size of mark 18 being ½ inch by ½ inch, then it is also preferred that any of marks 42–48 or 50–64 be no larger than ¾ inch by ¾ inch.

The construction or shape of the mark 18 is not important, e.g., it can be a star, square, circle, semicircle, diamond or the like. This also applies for the additional marks 42–48 and 50–64 in the vision field of the normal user. Again, these marks can be of any shape. In addition, marks 42–48 and 50–64 can contain numbers so as to obtain additional information from the tests as to the location of the loss of vision.

Furthermore, as previously detailed, the marks 14,18, 42–48 and 50–64 are preferably represented as contrast targets or objects. For example, mark 18 is a solid single color object of low contrast as shown in FIGS. 3–4; marks 42–48 and 50–64 are line figures having well defined shapes and low contrast as illustrated in FIGS. 2–4; and fixation target 14 as depicted in the drawings is a combination thereof.

As best illustrated in FIG. 4, there are four marks above horizontal line 26 and four marks below it, and each mark 50–64 is positioned outside the circular section 22 bounding the blind spot area 20. Also, the center of each of the additional marks 50–64 is positioned at a point wherein the angle $\beta$ is at least 20° removed from the horizontal base line 26, either clockwise or counterclockwise thereto. Furthermore, as illustrated, none of the additional marks 50–64 is positioned with its center positioned at a point wherein $\beta$ exceeds 170° in either a clockwise or a counterclockwise direction from the horizontal line 26. Although such placement of the additional marks is preferred; it should be recognized that these marks may be positioned up to 180° from the line 26, if desired.

The planar sheet 12 can be constructed of any suitable material including paper, board or other material preferably of light weight so that the device 10 formed therefrom can be made portable and can be held in one hand. The sheet 12 can be colored, but for ease of manufacture and contrast with the marks 18, 42–48 or 50–64 and non-interference with the fixation target 14, the sheet 12 normally will be white.

The fixation target 14 can be printed directly on the sheet 12 or can easily be positioned by affixing a target member to the sheet 12 with glue or the like so that it will remain in place during movement, storage and use of the present device 10. The fixation target 14 may be constructed from a reflective material, if desired, so that the user can see and maintain the reflection of his pupil in the fixation target 14. Examples of possible materials for such construction are milar, aluminum foil, glass and the like. It also may be advantageous to provide the fixation target 14 with a cross-hair 90, as best illustrated in FIG. 2, to assist the user in keeping the test eye 30 focused on the fixation target 14 throughout testing for glaucoma as required for proper testing. In order to accomplish the fixation of the eye on the fixation target 14, it also may be of assistance for the cross-hair 90 and its surroundings to be readily distinguishable; e.g., a black cross-hair on a white background, with the colors reversed at the point of the cross-hair. Other like contrasting combinations can be used in providing the fixation target 14.

As shown in FIGS. 1 and 2, for the convenience of the user, the device 10 can optionally have attached to one edge of the sheet 12, preferably at the sheet edge 92 closest to the fixation target, a measured length of material 94. The presence of this material 92 acting as a measuring element enables the user to easily and conveniently maintain the test eye 30 a proper predetermined distance D from the fixation target 14 throughout the test for glaucoma. Conveniently, this material 94 can be string, rope or the like.

In FIG. 5, another embodiment of the devices 10 of the present invention is illustrated wherein a single additional mark 96 is positioned on an arm 98. This arm 98 is affixed to the sheet 12 at the fixation target point 16 in a manner such that the arm 98 is adapted to pivot 360° about the point 16 so that the arm 98 can be rotated circumferentially to any position on the surface of the sheet 12. As the arm 98 is moved in the direction of either arrow A or B in FIG. 5 to positions such as those indicated in phantom at 98a–g in the drawings, the mark 96 is carried on the arm 98 so that the mark 96 is likewise circumferentially movable about the surface of the sheet 12 to various positions such as those indicated at 96a–g. Also, the object comprising the mark 96 may be moved radially inwardly or outwardly along the arm 98 as illustrated by arrow C in FIG. 5 in order to provide further flexibility in varying the positioning of the mark 96 about the surface of the sheet 12. Thus, mark 96 can be readily relocated for placement at a multiplicity of sites about the planar surface 12 in order to enable testing of glaucoma based on visibility of the mark 96 at various locations on the surface 12. However, it must be noted that as with the other devices described herein, the mark 96 must be positioned within the region corresponding to the normal field of peripheral vision of a test eye of a user of the device when the test eye is focused on the target 14 in order to enable a valid test procedure to be conducted with the device. This visible region corresponds to area 66 and lies within the same boundary lines between inner boundary 68 and outer boundary 70 or 74 as previously detailed.

Referring again to the drawings, FIG. 6 illustrates the use of the present device 10. In the performance of the test for glaucoma, the user shuts or shields a non-test eye so that vision therefrom is blocked, while focusing the pupil of the test eye 30 on the fixation target 14 from a predetermined distance D which in a hand-held version of the device 10 as shown in FIG. 6 may be established by moving the sheet 12 toward and away from the test eye 30 until the first mark 18 in the blind spot area 20 of the device 10 disappears from the view of the test eye 30 focused on the fixation target 14. In order to assist in this process, the optional measuring element 94 may be employed if desired, to determine and maintain the proper distance D between the test eye 30 and the fixation target 14 so that while the eye 30 is fixated on the fixation target 14, mark 18 will not be visible in the peripheral vision of the test eye 30. If this condition is met, then the user is assured that the test eye 30 and the device 10 are properly aligned and positioned to check for glaucoma in the test eye. The results of this testing depend on the visibility of the additional marks 42,44,46,48 as illustrated in the devices of FIGS. 1 and 2; 50,52,54,56,58,60,62,64 as illustrated in FIGS. 3 and 4; and 96 as illustrated in FIG. 5. If such marks are visible within the peripheral vision of the user of the device, then this result indicates that the user's test eye is not afflicted with glaucoma. However, if any of these marks 42,44,46, 48 or 50,52,54,56,58,60,62,64 or 96 are not visible or are indistinct, this indicates that professional advice should be sought at an early date in view of the detection of the signs of glaucoma.

In order to test the user's other eye utilizing the devices illustrated herein, the user turns the device 10 by 180° and repeats the procedure using the other eye. Additional areas can be tested with both eyes in a similar manner employing additional marks (not shown) on the reverse side of the device. Also, if desired, the device 10 may be constructed so that both eyes of a user of the device may be tested with an expanded display whereby inverting of the device 180° or reversal of the test sides of the card to test each eye will not be necessary.

Thus, the present device 10, which is preferably portable, can be used to self-determine the presence of glaucoma in each eye in a minimal time span without expensive equipment. This preliminary self-determination is extremely useful to enable the user to have a professional examination of his eyes performed prior to the spread of glaucoma. While it is not a replacement for a complete eye examination or formal visual field examination, it is an effective preliminary indicator to ascertain the possible existence of glaucoma in its earliest stages rather than waiting for the disease to spread and exhibit more advanced symptoms.

While specific embodiments of the invention have been shown and described, it will be obvious to those skilled in the art that changes and modifications may be made without departing from the spirit and scope of the invention as set forth in the following claims.

What is claimed is:

1. A method for self-detection of the presence of glaucoma in a human eye which comprises:

focusing an eye to be tested on a fixation target positioned on a planar surface, said surface also having a first mark formed and arranged thereon at a predetermined distance from said fixation target and one or more additional marks surrounding the first mark, positioning said test eye a sufficient separation distance from the fixation target and aligning said test eye relative to the fixation target to enable the testing of the user's peripheral vision by adjusting the distance and alignment of said test eye relative to said fixation target in reference to said first mark so that said first mark is in a blind spot area outside of the user's area of peripheral vision and is thereby removed from the user's field of vision when said test eye is positioned and aligned for testing;

maintaining said positioning of said test eye with said first mark removed from the field of vision of the test eye for the duration of the test in order to maintain the separation distance and the alignment of the test eye relative to the fixation target and to assure that the test eye remains focused on said fixation target at all times during the testing; and while maintaining said positioning of said test eye with the test eye focused on the fixation target and the first mark removed from the user's field of vision, determining the visibility of said additional marks employing the peripheral vision of the test eye whereby the presence of glaucoma is detected if said additional marks are not visible since the additional marks are formed and arranged on the planar surface to be within the field of vision of a user's eye not having glaucoma.

2. The method of claim 1 wherein each additional mark within the field of vision of the user is positioned within a region on the planar surface bounded by two concentric imaginary circular shapes each of which is defined as the intersection of an imaginary right circular cone with the planar surface, said right circular cones being formed by rotating imaginary lines of sight radiating from said test eye about an axis essentially perpendicular to the planar surface, said axis corresponding to an imaginary, substantially vertical line of sight between the test eye and the fixation target, the line of rotation forming the right circular cone corresponding to the inner of said two concentric circular shapes being an imaginary line of sight radiating from said test eye at an angle of about 10° relative to the vertical axis and the line of rotation forming the right circular cone corresponding to the outer of said two concentric circular shapes being an imaginary line of sight radiating from said test eye at an angle not greater than about 30° relative to the vertical axis.

3. The method of claim 1 wherein the distance between the eye and the fixation target is about 3 to about 4 times the distance between the fixation target and the first mark.

4. The method of claim 3 wherein the distance between the fixation target and the first mark is between about 2 and 6 inches.

* * * * *